US009662063B2

(12) United States Patent
Inui et al.

(10) Patent No.: US 9,662,063 B2
(45) Date of Patent: May 30, 2017

(54) PAIN SENSORY NERVE STIMULATION APPARATUS

(75) Inventors: Koji Inui, Okazaki (JP); Yasuyuki Takeshima, Okazaki (JP); Jun Motogi, Tokyo (JP); Yoshinobu Ono, Tokyo (JP); Ryosuke Ushijima, Tokyo (JP); Takeshi Kojima, Tokyo (JP)

(73) Assignees: INTER-UNIVERSITY RESEARCH INSTITUTE CORPORATION NATIONAL INSTITUTES OF NATURAL SCIENCES, Tokyo (JP); NIHON KOHDEN CORPORATION, Tokyo (JP)

( * ) Notice: Subject to any disclaimer, the term of this patent is extended or adjusted under 35 U.S.C. 154(b) by 200 days.

(21) Appl. No.: 13/587,050

(22) Filed: Aug. 16, 2012

(65) Prior Publication Data
US 2013/0053933 A1    Feb. 28, 2013

(30) Foreign Application Priority Data
Aug. 25, 2011    (JP) .................... 2011-183293

(51) Int. Cl.
*A61N 1/05*    (2006.01)
*A61B 5/00*    (2006.01)
*A61N 1/36*    (2006.01)

(52) U.S. Cl.
CPC .......... *A61B 5/4824* (2013.01); *A61N 1/0502* (2013.01); *A61N 1/36017* (2013.01); *A61N 1/36021* (2013.01)

(58) Field of Classification Search
CPC .............. A61N 1/0502; A61N 1/36017; A61N 1/36021; A61B 5/4824
USPC .......... 607/48, 46, 115, 148, 149, 152, 153
See application file for complete search history.

(56) References Cited

U.S. PATENT DOCUMENTS

| 4,747,841 | A | * | 5/1988 | Kuratomi | A61B 18/06 |
| | | | | | 424/447 |
| 5,296,225 | A | * | 3/1994 | Adekunle | A61K 9/0014 |
| | | | | | 424/484 |
| 7,781,486 | B2 | | 8/2010 | Szeles | |
| 2002/0077676 | A1 | * | 6/2002 | Schroeppel et al. | ............ 607/75 |
| 2004/0138712 | A1 | | 7/2004 | Tamarkin et al. | |
| 2006/0085056 | A1 | * | 4/2006 | Schouenborg | ................ 607/148 |
| 2007/0021803 | A1 | | 1/2007 | Deem et al. | |

(Continued)

FOREIGN PATENT DOCUMENTS

EP    2174589 A1    4/2010
JP    62-192141 A    8/1987

(Continued)

OTHER PUBLICATIONS

Office Action dated Mar. 31, 2015, issued by the Japanese Patent Office in counterpart Japanese Application No. 2011-183293.

(Continued)

*Primary Examiner* — Michael Carey
(74) *Attorney, Agent, or Firm* — Sughrue Mion, PLLC

(57) ABSTRACT

A pain sensory nerve stimulation apparatus includes: a stimulation electrode which is adapted to be attached to a living body, at least one of an exogenous algesic substance and pyrogen which is to be interposed between the living body and the stimulation electrode; and a stimulation power supplier which is configured to supply electric power to the stimulation electrode.

7 Claims, 5 Drawing Sheets

(56) References Cited

U.S. PATENT DOCUMENTS

| | | |
|---|---|---|
| 2007/0219286 A1* | 9/2007 | Ishii .............................. 523/111 |
| 2008/0255634 A1 | 10/2008 | Jaax et al. |
| 2008/0269847 A1 | 10/2008 | Nemenov |
| 2009/0149693 A1 | 6/2009 | Dacey, Jr. et al. |
| 2010/0094378 A1* | 4/2010 | Inui .................... A61B 5/04001 |
| | | 607/46 |
| 2010/0228304 A1 | 9/2010 | Kriksunov et al. |
| 2011/0112605 A1* | 5/2011 | Fahey .................. A61N 1/0452 |
| | | 607/48 |
| 2011/0196256 A1 | 8/2011 | Inui et al. |

FOREIGN PATENT DOCUMENTS

| | | |
|---|---|---|
| JP | 2010088802 A | 4/2010 |
| JP | 2011164879 A | 8/2011 |
| WO | 2010024491 A1 | 3/2010 |

OTHER PUBLICATIONS

Communication dated Jan. 3, 2013 from the European Patent Office in counterpart European application No. 12179686.6.

Office Action dated Dec. 28, 2016 issued by the State Intellectual Property Office of P.R. China in counterpart Chinese Patent Application No. 201210308562.3.

* cited by examiner

PAIN SENSORY NERVE STIMULATION APPARATUS

BACKGROUND OF THE INVENTION

The present invention relates to a pain sensory nerve stimulation apparatus which can adequately perform selective stimulation of desired nerve fibers (particularly, C fibers) of a living body.

As described in JP-A-2010-088802, in order to early detect a disorder of peripheral nerve which is one of the three major complications of diabetes, a method in which only C fibers are stimulated and a reaction to the stimulation is checked is highly requested.

JP-A-2010-088802 discloses a pain sensory nerve stimulation apparatus which can stimulate only C fibers. In the proposed apparatus, only C fibers can be selectively stimulated, and various applications are expected. Also in the case where stimulation is performed by the pain sensory nerve stimulation apparatus, however, there are individual variations, and, even for healthy individuals, different reactions to the same stimulation intensity (mA) sometimes occur.

JP-A-2010-088802 discloses that, when the stimulation intensity based on the current amount is low, C fibers are stimulated, and, as the stimulation intensity becomes higher, thicker fibers such as Aδ fibers are stimulated. However, there are individual variations in sensitivity to stimulation. When the stimulation intensity is increased, therefore, desired fibers cannot be stimulated. Moreover, a stimulation intensity based on a large current amount causes the subject to feel pain. Therefore, a stimulation technique may be possible in which, in the initial stage of measurement, stimulation is started at an intensity based on a small current amount, and then gradually changed to have an intensity based on a large current amount.

According to the stimulation technique, however, the reaction becomes duller as time progresses, or the reaction becomes hypersensitive with the elapse of time, thereby causing a problem in that an adequate result cannot be obtained. In the case where only C fibers are to be selectively stimulated as disclosed in JP-A-2010-088802 discloses, particularly, stimulation must be performed by using a very weak current, and, depending on the skill of the inspector, the stimulation may not be adequately performed, so that the inspection sometimes fails to be done well.

U.S. Pat. No. 7,781,486 discloses a technique in which, in order to intensify the action of stimulation using a needle electrode, a substance inhibiting the enzymatic decomposition of endogenous opioide is administered in the form of an intravenous infusion. In the technique, an intravenous infusion is required. Therefore, the technique has a drawback that the technique cannot be simply used for applying stimulus.

SUMMARY

The invention provides a pain sensory nerve stimulation apparatus which, without using a stimulation intensity based on a large current amount, can selectively stimulate desired nerve fibers (particularly, C fibers) of a living body in an adequate and simple manner.

An aspect of the invention provides a pain sensory nerve stimulation apparatus comprising: a stimulation electrode which is adapted to be attached to a living body, at least one of an exogenous algesic substance and pyrogen which is to be interposed between the living body and the stimulation electrode; and a stimulation power supplier which is configured to supply electric power to the stimulation electrode.

The stimulation electrode may include: a first electrode, a tip end of which is adapted to be inserted into a skin; and a second electrode, which is disposed in a circumference of the first electrode without being electrically conductive with the first electrode, and which is adapted to be in contact with a skin of the living body. The stimulation power supplier may supply a pulse signal in which an electrical polarity of the first electrode is set as one of an anode and a cathode, and an electrical polarity of the second electrode is set as the other of the anode and the cathode.

The exogenous algesic substance may include at least one of capsaicin, sanshool, zingerone, camphor, allyl isothiocyanate, and menthol.

The pyrogen may use heat generation due to an oxidation reaction of a metal.

The at least one of the exogenous algesic substance and the pyrogen may be provided integrally with the stimulation electrode.

The at least one of the exogenous algesic substance and the pyrogen may be interposed after being diluted with vaseline.

The stimulation power supplier may supply, to the stimulation electrode, the electric power for selectively stimulating desired nerve fibers of the living body.

DETAILED DESCRIPTION OF EMBODIMENTS

Figure 1:
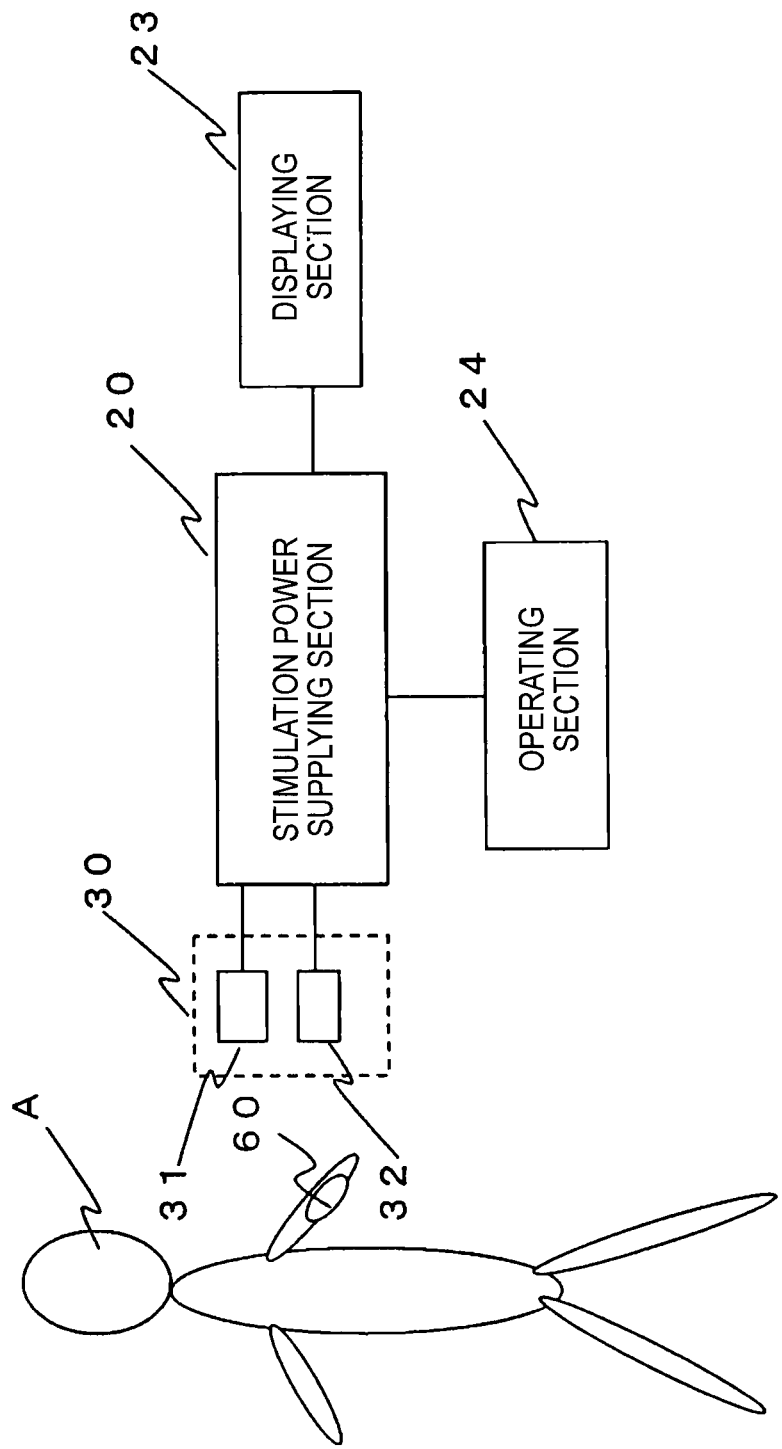
FIG. 1 is a block diagram illustrating the configuration of an embodiment of the pain sensory nerve stimulation apparatus of the invention.

Hereinafter, an embodiment of the pain sensory nerve stimulation apparatus of the invention will be described with reference to the accompanying drawings. In the figures, the identical components are denoted by the same reference numerals, and duplicated description will be omitted. FIG. 1 is a diagram of the embodiment of the pain sensory nerve stimulation apparatus. The pain sensory nerve stimulation apparatus includes a stimulation electrode 30 which is to be attached to a living body A.

Figure 2:
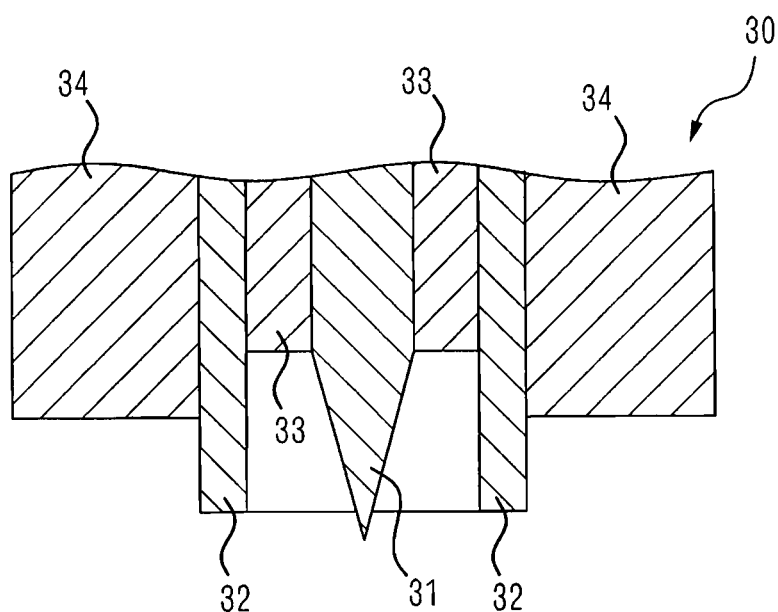
FIG. 2 is a sectional view illustrating a stimulation electrode used in the embodiment of the pain sensory nerve stimulation apparatus of the invention.
Figure 3:
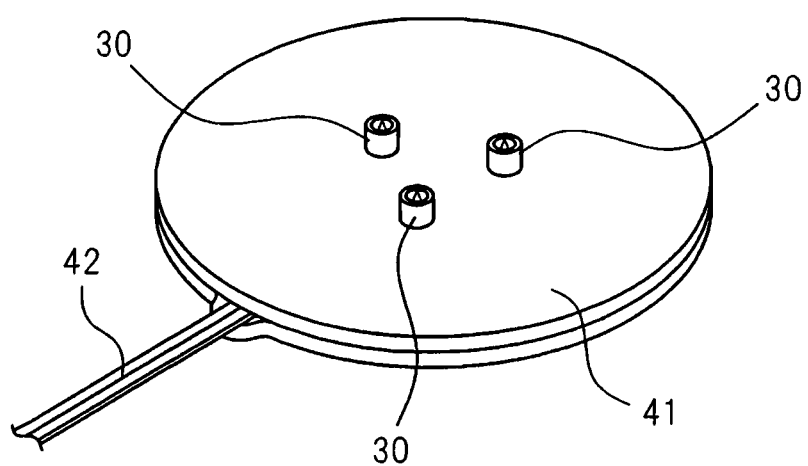
FIG. 3 is a perspective view illustrating a part of a modification of the stimulation electrode used in the embodiment of the pain sensory nerve stimulation apparatus of the invention.

For example, the stimulation electrode 30 is configured so as to have a section shown in FIG. 2. The stimulation electrode 30 includes a needle electrode 31 functioning as a first electrode in which the tip end has a shape that allows the tip end to be slightly inserted into the skin, and a contact electrode 32 functioning as a second electrode which is to be used while being in contact with the skin. As seen from FIG. 2, the needle electrode 31 is projected with respect to the contact electrode 32. The tip end of the needle electrode 31 is not always necessary to be pointed, and may have a spherical or rod-like shape. The contact electrode 32 may have a cylindrical shape which surrounds the needle electrode 31 while being centered at the needle electrode 31, or alternatively a plurality of contact electrodes 32 may be cylindrically placed so as to be centered at the needle electrode 31. The contact electrode has an inner diameter of, for example, 1 mm.

Alternatively, a part of the contact electrode 32 has a shape which can be slightly inserted into the skin. A spacer 33 configured by an insulating material may be embedded in the gap between the contact electrode 32 and the needle electrode 31. An external fitting section 34 which has a columnar shape using the contact electrode 32 as a core, and which is formed by an insulating material is disposed in the circumference of the contact electrode 32.

Figure 4:
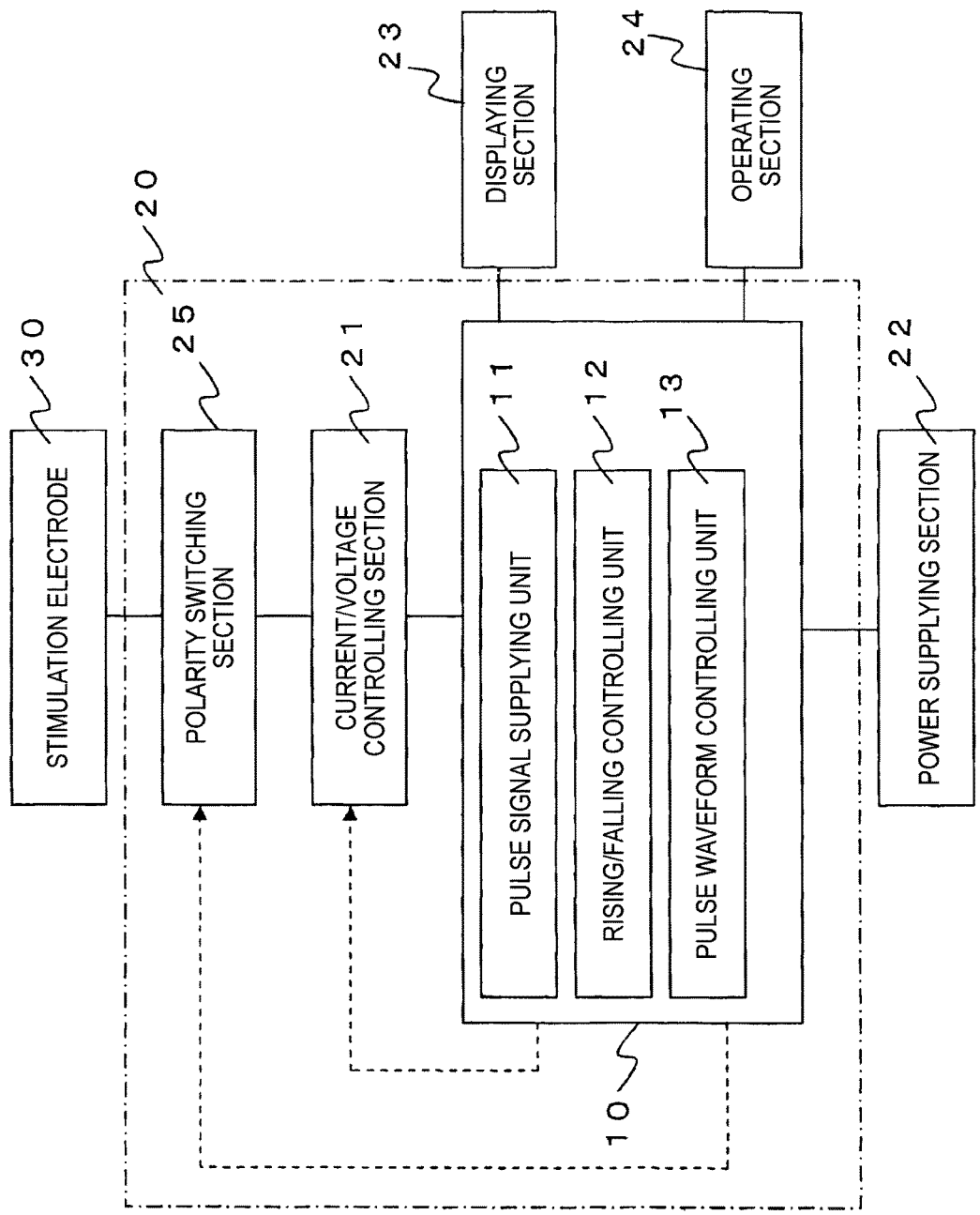
FIG. 4 is a block diagram of a part of the embodiment of the pain sensory nerve stimulation apparatus of the invention.

A configuration may be employed where, as shown in FIG. 4, a plurality (in this example, three pairs (poles)) of stimulation electrodes 30 each formed by a pair of the contact electrode 32 and needle electrode 31 which are indicated in FIG. 2 are used, the stimulation electrodes stand on a disk-like base 41 made of an insulating resin, and the three needle electrodes 31 are connected to one conductive wire, and the three contact electrodes 32 to one conductive wire to be led out as lead wires 42.

Even when any one of the above-described configurations of the stimulation electrode 30 is used, at least one of an exogenous algesic substance 60 and a pyrogen 60 is interposed between the stimulation electrode 30 and the contact portion of the living body A, by means of, for example, application (FIG. 1). Examples of the exogenous algesic substance 60 are capsaicin, sanshool, zingerone, camphor, allyl isothiocyanate, and menthol. The exogenous algesic substance is a concept which contains an algesic substance, a phlogogenic substance, and an irritating substance. In the case where the exogenous algesic substance 60 is interposed by means of application, it is preferably applied about 20 minutes before stimulation of the living body. Preferably, the pyrogen 60 warms the stimulation portion of the living body A to about 30° C. by, for example, using heat generation due to an oxidation reaction of a metal.

The stimulation electrode 30 is connected to a stimulation power supplying section 20. The stimulation power supplying section 20 supplies an electric power for stimulating only C fibers in the living body, and specifically performs a power supply while changing the electrical polarity of a pulse. The configuration of the stimulation power supplying section is similar to that disclosed in JP-A-2010-088802, and as shown in FIG. 4.

Namely, the stimulation power supplying section 20 has a configuration in which a current/voltage controlling section 21 is connected to a pulse generation body unit 10, and a polarity switching section 25 is connected to the current/voltage controlling section 21. The stimulation electrode 30 is connected to the polarity switching section 25. A power supplying section 22 supplies electric power to various portions.

The pulse generation body unit 10 is configured by an analog/digital microprocessor, and includes a pulse signal supplying unit 11 which generates and supplies a pulse signal, a rising/falling controlling unit 12, and a pulse waveform controlling unit 13. The rising/falling controlling unit 12 changes at least one of the rising and falling times of the pulse signal supplied from the pulse signal supplying unit 11.

The rising/falling controlling unit 12 can select either of a rectilinear mode where the rise or fall of the pulse signal has a rectilinearly rising and falling shape, and an exponential mode where the rise or fall of the pulse signal has an exponentially rising and falling shape, so that a pulse waveform having a required shape can be produced.

The current/voltage controlling section 21 connected to the pulse generation body unit 10 is a stimulation intensity controlling unit which changes at least one of the voltage and current of the pulse signal supplied from the pulse signal supplying unit 11. The polarity switching section 25 connected to the current/voltage controlling section 21 functions as an electrical polarity converting unit which converts the electrical polarity of the needle electrode 31 and that of the contact electrode 32.

An operating section 24 includes a pulse waveform setting unit. The pulse waveform setting unit can set the pulse waveform controlling unit 13 so that the pulse signal is changed to have desired pulse width, pulse interval, and pulse number. The operating section 24 includes a stimulation intensity setting unit. The stimulation intensity setting unit enables the current/voltage controlling section 21 which is the stimulation intensity controlling unit, to change the pulse signal to have a desired current or voltage.

The operating section 24 includes a polarity conversion setting unit. The polarity conversion setting unit can give instructions for causing the polarity switching section 25 which is the electrical polarity converting unit, to convert the electrical polarity. According to the configuration, the electrical polarity of the needle electrode 31 can be set as the anode, and that of the contact electrode 32 can be set as the cathode, or, by contrast, the electrical polarity of the needle electrode 31 can be set as the cathode, and that of the contact electrode 32 can be set as the anode. As seen also from JP-A-2010-088802, in the case where the electrical polarity of the needle electrode 31 is set as the anode, C fibers can be selectively stimulated. In the case where the polarity switching section 25 sets the electrical polarity of the needle electrode 31 as the cathode, moreover, Aδ fibers can be selectively stimulated.

The operating section 24 connected to the stimulation power supplying section 20 is operated so as to give: an instruction input for causing the rising/falling controlling unit 12 to change the pulse signal to have desired rising and falling times; instructions for causing the pulse waveform controlling unit 13 to change the pulse signal to have desired pulse width, pulse interval, and pulse number; and instructions for causing the current/voltage controlling section 21 to change the pulse signal to have a desired current or voltage. From the display on a displaying section 23 connected to the stimulation power supplying section 20, it is checked whether desired settings are performed by the operating section 24 or not, and an operation of starting stimulation can be then performed. As described above, the operating section 24 includes a setting unit which sets, with respect to the pulse signal, at least one of the stimulation intensity (mA), the rising and falling times of the pulse, the pulse width, the pulse interval, the pulse number, the pulse shape, and the electrode polarity. Of course, the stimulation by the stimulation power supplying section 20 may be caused by applying, between the first and second electrodes, a bipolar stimulation signal configured by a combination of a first waveform signal which, in the first electrode, is convex in the negative direction, and a second waveform signal which, in the first electrode, is convex in the positive direction, in a manner similar to the stimulation disclosed in JP-A-2011-164879.

Table 1 indicates results of measurements in which an appropriate amount (a weight ratio of about 0.05 to 0.1 with respect to vaseline) of capsaicin was applied as the exogenous algesic substance to four subjects. Table 1 indicates relationships between the current threshold in the case where the anode stimulation was performed on each subject and C fibers of each subject was stimulated, and the time period elapsed after the application.

It is known that, although there are individual variations, the current threshold substantially has a downward trend during 20 minutes after the application of the exogenous algesic substance. Particularly, it is known that, in Subject 2, the current threshold is largely reduced to about one half of the normal value, and, in Subject 3, to about two thirds of the normal value. Since an effect due to stimulation was obtained even at a low stimulation intensity (mA), this minimizes the burden on a subject, and realizes the check of the nerve function. It was also confirmed that an effective examination can be conducted without being affected by the skill of the measuring person.

TABLE 1

| Time period after application | Subject 1 | Subject 2 | Subject 3 | Subject 4 |
|---|---|---|---|---|
| 5 minutes | 0.10 (mA) | 0.32 (mA) | 0.14 (mA) | 0.05 (mA) |
| 10 minutes | 0.10 (mA) | 0.18 (mA) | 0.13 (mA) | 0.04 (mA) |
| 15 minutes | 0.09 (mA) | 0.13 (mA) | Unknown | 0.04 (mA) |
| 20 minutes | 0.09 (mA) | 0.15 (mA) | 0.09 (mA) | 0.04 (mA) |

Figure 5A:
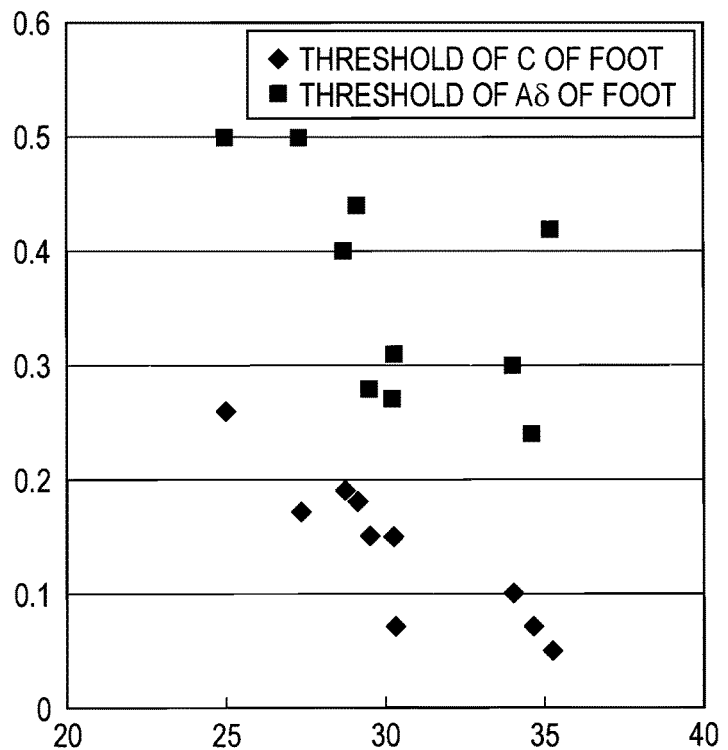
FIGS. 5A and 5B are views illustrating measurement results in the case where stimulation was performed by the embodiment of the pain sensory nerve stimulation apparatus of the invention.
Figure 5B:
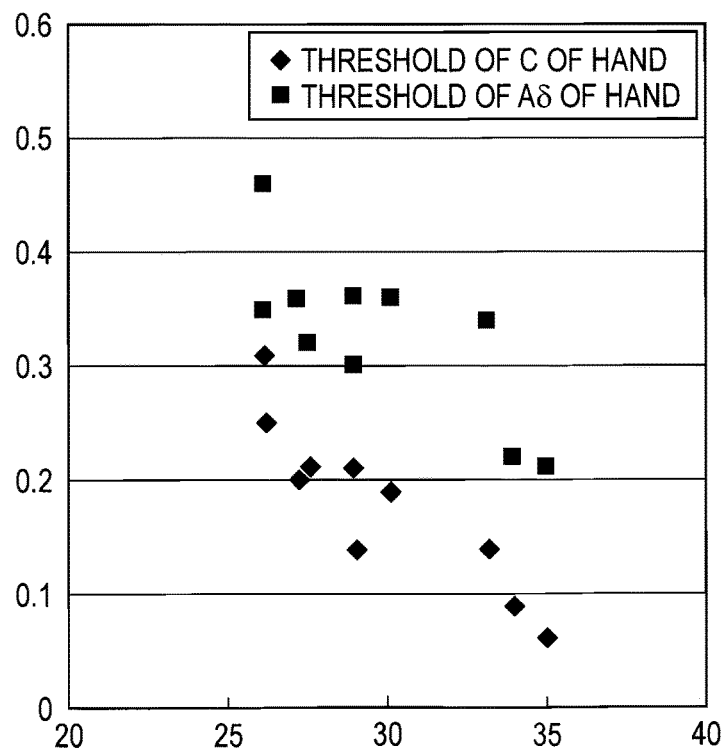

Next, FIGS. 5A and 5B illustrate relationships between the temperature of the simulation portion and the current threshold. The foot and the hand are employed as simulation portions. FIGS. 5A and 5B illustrate results of measurements performed on the foot and the hand, respectively. In the figures, the abscissa indicates the current threshold (mA) in the case where C fibers or Aδ fibers were stimulated, and the ordinate indicates the temperature of the simulation portion. As seen from FIGS. 5A and 5B, it can be confirmed that, even at different simulation portions, the current threshold tends to be smaller in accordance with the temperature rise of the simulation portion. When the temperature of the simulation portion is raised, therefore, an effect due to stimulation is obtained even at a low stimulation intensity (mA), the burden on a subject is minimized, and also the check of the nerve function is realized.

In the case where the exogenous algesic substance 60 and/or the pyrogen 60 is used, it may be used after being diluted with vaseline or the like. The stimulation intensity may be changed in accordance with the degree of the dilution. Alternatively, the stimulation intensity may be changed correspondingly with the kind of the exogenous algesic substance 60 and/or the pyrogen 60. With respect to the stimulation intensity, the apparatus may be configured so that preset values are previously stored correspondingly with the kind or dilution degree of the exogenous algesic substance 60 and/or the pyrogen 60, in a storage section of the pulse generation body unit 10, and read out and displayed on the displaying section 23 in the form of data of a list in response to an operation on the operating section 24, and a desired stimulation intensity is selected. Furthermore, the exogenous algesic substance 60 and/or the pyrogen 60 may be formed integrally with the stimulation electrode 30, so that effective stimulation can be performed only by attaching the stimulation electrode 30 to the subject, rapidly and irrespective of the skill of the measuring person. Therefore, the configuration is very useful.

According to an aspect of the invention, at least one of the exogenous algesic substance and the pyrogen is interposed between the living body and the stimulation electrode, and the electric power for selectively stimulating desired nerve fibers of the living body is supplied to the stimulation electrode. In a state where stimulation is appropriately applied by at least one of the exogenous algesic substance and the pyrogen, C fibers, Aδ fibers, and the like can be selectively stimulated in an adequate and simple manner, without using a stimulation intensity based on a large current amount.

According to an aspect of the invention, the stimulation electrode includes: the first electrode which is to be used while the tip end is slightly inserted into a skin; and the second electrode which is placed in the circumference of the first electrode without being electrically conductive with the first electrode, and which is to be used while being in contact with the skin, and the stimulation power supplier supplies the pulse signal in which the electrical polarity of the first electrode is one of the anode and cathode, and that of the second electrode is the other of the anode and cathode. When stimulation is performed while setting the electrical polarity of the first electrode as the anode, therefore, C fibers can be selectively stimulated, and, when stimulation is performed while setting as the cathode, Aδ fibers can be selectively stimulated.

According to an aspect of the invention, the exogenous algesic substance includes at least one of capsaicin, sanshool, zingerone, camphor, allyl isothiocyanate, and menthol, and the interposition is performed about 20 minutes before stimulation of a stimulation portion, whereby stable and effective stimulation can be performed.

According to an aspect of the invention, the pyrogen uses heat generation due to an oxidation reaction of a metal, whereby the stimulation portion can be warmed at an adequate temperature, so that stable and effective stimulation can be performed.

According to an aspect of the invention, the at least one of the exogenous algesic substance and the pyrogen is formed integrally with the stimulation electrode. Therefore, stable and effective stimulation can be performed rapidly and irrespective of the measuring person.

According to an aspect of the invention, the at least one of the exogenous algesic substance and the pyrogen is interposed after being diluted with vaseline, whereby the influence of the one of the exogenous algesic substance and the pyrogen on the living body is mitigated. Therefore, stable and effective stimulation can be performed while reducing the burden on the subject.

What is claimed is:

1. A pain sensory nerve stimulation apparatus comprising:
a stimulation electrode device which is adapted to be attached to a living body, the stimulation electrode device including:
a first electrode comprising a tip end, wherein the tip end is adapted to be inserted into a skin of the living body; and
a second electrode, which surrounds a circumference of the first electrode without being electrically conductive with the first electrode, and which is adapted to be in contact with a skin of the living body;
at least one of an exogenous algesic substance and pyrogen which is to be interposed between the living body and at least a portion of the stimulation electrode device, wherein the exogenous algesic substance contains an algesic substance, a phlogogenic substance or an irritating substance; and
a stimulation power supplier which is configured to supply electric power to the stimulation electrode device, and which is configured to supply a pulse signal to each of the first electrode and the second electrode within 20 minutes from interposition of the at least one of the exogenous algesic substance and the pyrogen, the stimulation power supplier configured to change at least one of a voltage and a current of the pulse signal to selectively stimulate Aδ fibers or C fibers in a state where the tip end of the first electrode is adapted to be inserted into the skin of the living body and the second electrode is adapted to be in contact with the skin of the living body, wherein, when an electrical polarity of the first electrode is set as an anode and an electrical polarity of the second electrode is set as a cathode, only the C fibers are stimulated, and when an electrical polarity of the second electrode is set as an anode and the electrical polarity of the first electrode is set as a cathode, only the Aδ fibers are stimulated.

2. The pain sensory nerve stimulation apparatus according to claim 1, wherein the exogenous algesic substance includes at least one of capsaicin, sanshool, zingerone, camphor, allyl isothiocyanate, and menthol.

3. The pain sensory nerve stimulation apparatus according to claim 1, wherein the pyrogen uses heat generation to warm a stimulation portion of the living body, due to an oxidation reaction of a metal of the at least one of the exogenous algesic substance and the pyrogen.

4. The pain sensory nerve stimulation apparatus according to claim 1, wherein the at least one of the exogenous algesic substance and the pyrogen is provided integrally with the stimulation electrode device.

5. The pain sensory nerve stimulation apparatus according to claim 1, wherein the at least one of the exogenous algesic substance and the pyrogen is interposed after being diluted with vaseline.

6. The pain sensory nerve stimulation apparatus according to claim 1, wherein the stimulation power supplier supplies, to the stimulation electrode device, the electric power for selectively stimulating desired nerve fibers of the living body.

7. The pain sensory nerve stimulation apparatus according to claim 1, further comprising a displaying section configured to display preset values corresponding to the at least one of the exogenous algesic substance and pyrogen, the preset values being displayed on the displaying section for selecting a desired stimulation intensity.

* * * * *